United States Patent [19]

Lee

[11] Patent Number: 5,132,119
[45] Date of Patent: Jul. 21, 1992

[54] TREATMENT OF HYPERTROPHIC WOUND HEALING DISORDERS WITH CALCIUM CHANNEL BLOCKERS

[75] Inventor: Raphael C. Lee, Chicago, Ill.

[73] Assignee: Massachusetts Institute of Technology, Cambridge, Mass.

[21] Appl. No.: 629,080

[22] Filed: Dec. 17, 1990

Related U.S. Application Data

[63] Continuation of Ser. No. 387,604, Jul. 31, 1989, abandoned.

[51] Int. Cl.$^5$ .................. A61K 31/275; A61K 31/44; A61K 33/24
[52] U.S. Cl. .................................. 424/646; 514/277; 514/356; 514/523; 514/947
[58] Field of Search ............... 514/277, 356, 501, 654, 514/523; 424/646

[56] References Cited

FOREIGN PATENT DOCUMENTS 52-025768 2/1977 Japan .
52-083545 7/1977 Japan .

OTHER PUBLICATIONS

McLeod, Kenneth J., "Modulation of Biosynthesis by Physiologically Relevant Electric Fields", PhD Thesis, Massachusetts Institute of Technology, Feb., 1986.
Askey, D. B. et al., J. Cell Biol., Joint Meeting of American Society for Cell Biol. and American Society for Biochem. and Mol. Bio., San Francisco, Calif., Abt. #1905, p. 336a, Jan. 29–Feb. 2, 1989.
Askey, D. B. et al., *Proceedings Electrochemical Society*, Los Angeles, Calif., May 7–12, 1989.
Ohmori, S., *Aesthetic Plastic Surgery* 12:95–99 (1988).
Chen, C. et al., *Science* 239:1024–1026 (1988).
Onuma, E. K. and S.-W. Hui, *J. Cell Bio.* 106:2069–2075 (1988).
McLeod, K. J. et al., *Science* 236:1465–1469 (1987).
Abergel, R. P. et al., *J. Invest. Dermatol.* 84:384–390 (1985).
Miller, E. A., "Electric Field Modulation of Exocytosis in Human Fibroblasts", S.B. Thesis, M.I.T. (1987).
Sank, A. et al., *Surgery* 106:1141–1148 (Dec. 1989).
Steinleitner, A. et al., *J. Reproductive Medicine*, 33:891–894 (Nov. 1988).
Block, L. H. et al., *Proc. Natl. Acad. Sci. USA* 86:2388–2392 (Apr. 1989).
Lee, R. C. and J. Ping, *J. Surg. Res.* 49:463–466 (1990).

Primary Examiner—Mukund J. Shah
Assistant Examiner—Philip I. Datlow
Attorney, Agent, or Firm—Hamilton, Brook, Smith & Reynolds

[57] ABSTRACT

This invention pertains to a method for controlling hypertrophic wound healing disorders by administering calcium channel blockers to the wound site. Calcium channel blockers are found to regulate fibroblast biosynthesis and can therefore be used to therapeutically control diseases characterized by excessive fibroblast biosynthesis.

12 Claims, 4 Drawing Sheets

TREATMENT OF HYPERTROPHIC WOUND HEALING DISORDERS WITH CALCIUM CHANNEL BLOCKERS

This is a continuation of co-pending application Ser. No. 07/387,604 filed on Jul. 31, 1989 now abandoned.

BACKGROUND OF THE INVENTION

A hypertrophic scar is an excessive wound scar which by definition has grown in size beyond that required for normal wound healing. Hypertrophic scars can emerge from many wound types, such as from a burn or a sharp incision. Keloids, a more severe form of hypertrophic wound scars, form firm dermal nodules of scar which are most commonly preceded by trauma at the site of origin. They are usually larger than hypertrophic scars and differ in that they frequently invade the normal skin adjacent to the wound.

Hypertrophic scars and keloids result from an overproduction of cells, collagen and proteoglycan [Linares, H. A. and Larson, D. L., *Plast. Reconst. Surg.*, 62:589 (1978); Linares, H. A., *Plast. Reconstr. Surg.*, 818-820 (1983)]. Histologically, these lesions are characterized by randomly distributed tissue bundles consisting of uniaxially oriented extracellular matrix and cells. In these scars, the overproduction and compaction of collagen and proteoglycans [Shetlar, M. R. et al., *Burns* 4:14 (1977)] exceeds the proliferation of cells. These histological observations suggest that the lesions result from loss of the normal control mechanisms which regulate the synthesis of extracellular matrix during would healing [Shetlar. M. R. et al., *Burns* 4:14 (1977)].

Existing therapy for hypertrophic scars and keloids, includes surgery, mechanical pressure, steroids, x-ray irradiation and cryotherapy. There are many disadvantages associated with each of these methods. Surgical removal of the scar tissue is often incomplete and can result in the development of hypertrophic scars and keloids at the incision and suture points. Steroid treatments are unpredictable and often result in depigmentation of the skin. X-ray therapy is the only predictably effective treatment to date; however, because of its potential for causing cancer, it is not generally recommended or accepted.

Compositions comprising tripeptides, tetrapeptides and pentapeptides have been shown to inhibit biosynthesis of collagen and may be used to treat diseases caused by excess accumulation of collagen (Mitsubishi Chem., Japanese Patent Nos. 52083545, Jul. 12, 1977, and 52025768, Feb. 25, 1977).

Recently, the effects of applying silastic sheets onto the surface of hypertrophic scars was studied and shown to shrink and soften scar tissue. [Ohmori, S. *Aesthetic Plastic Surgery* 12:95-99 (1988)].

Despite the various treatments presently available, there is no widely accepted and predictably effective means for preventing or treating hypertrophic scars or keloids.

SUMMARY OF THE INVENTION

This invention pertains to a method for minimizing hypertrophic wound healing disorders, such as hypertrophic scars and keloids. Specifically, the method comprises administering an effective amount of a calcium channel blocking agent to a hypertrophic scar site for a period of time sufficient to minimize the wound or scar. Preferably, the calcium channel blocking agent is selected from verapamil, biologically compatible cobalt salts, such as cobalt chloride, and hydropyridine compounds, such as nifedipine. The calcium channel blocking agent is applied to the wound site, such as by injecting it directly into a scar or topically applying it onto the wound site. In either case, the calcium channel blocking agent can be admixed with a pharmaceutically acceptable vehicle to facilitate localization of the agent to the wound site. The drug may be put into sustained release capsules to provide continuous treatment at therapeutic doses without systemic side effects.

This invention further pertains to a method for regulating and/or inhibiting exocytosis in fibroblast cells. The method comprises contacting fibroblast cells with an effective concentration of a calcium channel blocking agent sufficient to reduce exocytosis or even inhibit exocytosis.

The method of the present invention can be used to minimize hypertrophic wound healing disorders in humans. The method may also be used to treat other mammals. It can also be used to prevent formation of excessive tissue scarring. Alternatively, a calcium channel blocking agent can be applied to a presently existing hypertrophic scar to reverse the scarring process and essentially eliminate the scar tissue. The present invention can also be used therapeutically to control diseases associated with excessive fibroblast biosynthesis, such as cirrhosis of the liver, constrictive pericarditis, Dupuytren's disease of the hand, plantar fibrosis of the foot and various other fibromastosis.

DETAILED DESCRIPTION OF THE INVENTION

Figure 1A:
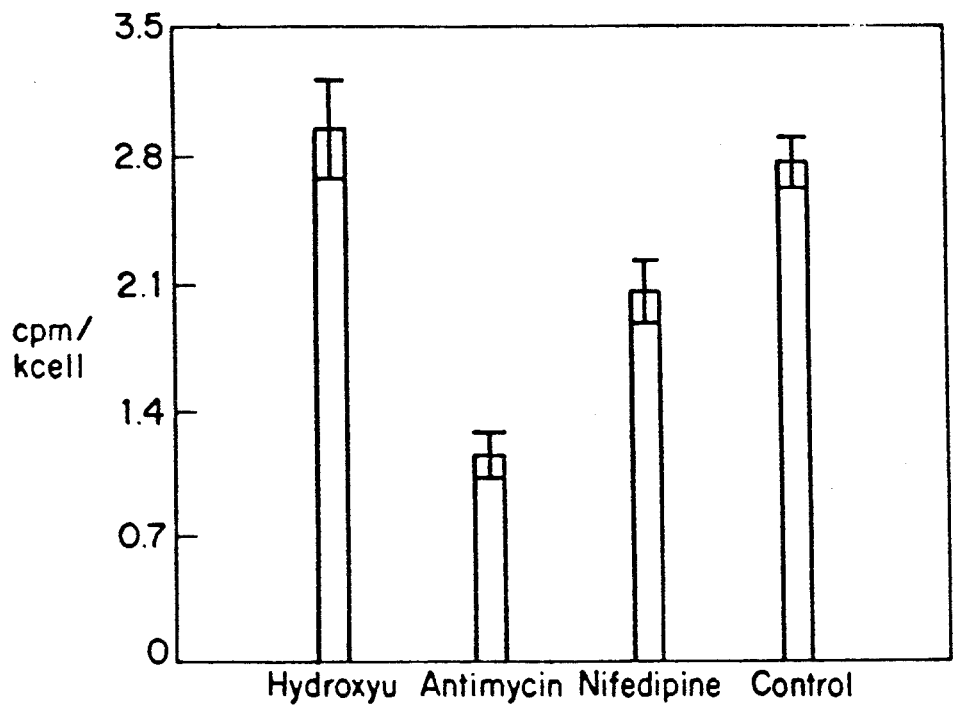
FIG. 1a is graphic representation of the effects of hydroxyurea (7.9 mM), antimycin A (1.0 $\mu$M) and nifedipine (100 $\mu$M) on the rate of proline incorporation into fibroblast populated collagen matrices (FPCM) bathed in DMEM/5.5 mM fructose.

Calcium channels are regions of cell membranes which facilitate the transport and secretion of fluids and electrolytes, such as calcium, into the cell [Rasmussen, H. *N.E. J. Med.* 314:1094-1101 (1986)]. These channels can be blocked using a class of compounds known as calcium channel blockers or calcium entry blockers. Compounds included in this class are verapamil, cobalt chloride and other biologically acceptable salts of cobalt, and hydropyridine compounds, such as nifedipine.

The present invention is based upon the discovery that calcium channel blocking drugs, which block the transport of calcium across the cell membrane, can inhibit exocytosis in fibroblast cells; can retard biosynthesis of collagen and sulfated glycosaminoglycans (GAG); and can be used to decrease the collagen content of the extracellular matrix.

Exocytosis is a process involved in cellular secretion of protein. During secretion, vesicles that contain sorted and concentrated protein pinch off from the Golgi apparatus and move toward the cell membrane at the leading edge of the cell, where they fuse with the cell membrane and release protein into the extracellular space. This process of fusion and release is known as exocytosis and is an essential step in secretion of extracellular matrix macro-molecules (such as glycosaminoglycans, collagen and elastin). Many diseases and disorders are brought about as the result of excessive biosynthesis. For example, hypertrophic wound healing disorders are characterized by over secretion of protein and collagen. The over-production results in excessive scarring or keloid formation.

As a result of the present discovery that calcium channel blockers can inhibit exocytosis in fibroblasts, the invention can be used to prevent, minimize or even eliminate these hypertrophic wound healing disorders by reducing fibroblast secretion of protein and glycosaminoglycans. Fibroblast secretion is blocked when exocytosis is inhibited. Likewise, other diseases in which the cells undergo excessive fibroblast secretion can be therapeutically controlled using the methods of this invention.

In a preferred embodiment, hypertrophic wounds can be minimized by administering an effective amount of a calcium channel blocker to a hypertrophic wound site for a period of time sufficient to minimize the wound area. Suitable calcium channel blockers include, but are not limited to verapamil, biologically acceptable salts of cobalt, such as cobalt chloride, and hydropyridine compounds, such as nifedipine. The amount of calcium channel blocker which can be effectively administered is dependent upon the type of calcium channel blocker used. Threshold effective amounts of verapamil and nifedipine are approximately 10 $\mu$M and 100 $\mu$M, respectively.

Hydropyridine compounds, such as nifedipine are relatively insoluble in aqueous solution. Due to their insolubility, it may be advantageous to solubilize the drug in a non-polar carrier depending upon the location of the disorder to be treated. Calcium channel blockers can be administered to a wound site either alone or they can be admixed with pharmaceutically acceptable vehicles to facilitate their diffusion into the wound site. One suitable vehicle is dimethyl sulfoxide in a physiologically acceptable amount. Calcium channel blockers can be incorporated into liposomes.

Calcium channel blockers can be concentrated and incorporated into controlled release polymers as an alternative mode of administering the drug (e.g., transdermal administration). Examples of controlled release polymers have been described by Folkman and Langer, U.S. Pat. No. 4,391,727, issued Jul. 5, 1983; Yolles, U.S. Pat. Nos. 3,880,991, issued Apr. 29, 1975, and 3,887,699, issued Jun. 3, 1975; Boswell, U.S. Pat. No. 3,773,919, the teachings of which are incorporated herein by reference. Preferably, biodegradable polymers will be used.

The method of administering an acceptable dose of calcium channel blocker to minimize scarring is dependent upon the location of the hypertrophic wound and the extent of scarring. In particular, the calcium channel blocker, either alone or in combination with a pharmaceutically acceptable vehicle, can be topically applied to the surface of the wound site; it can be injected into the wound site, or it can be incorporated into a controlled release polymer and surgically implanted in a region to be treated. Surgical implantation is advantageous for treating disorders such as cirrhosis of the liver and constrictive pericarditis. This permits the calcium channel blocker to be localized in the diseased site without adversely effecting the patient or releasing excessive amounts of the drug into the circulation system.

Exocytosis of fibroblast cells can be regulated or even prevented using the methods of this invention. In particular, fibroblasts are contacted with an effective amount of a calcium channel blocker sufficient to retard exocytosis to a desired degree. The method of contacting the calcium channel blockers to the fibroblast cells of interest and the effective amount of these drugs are described above.

In addition to treating hypertrophic wound healing disorders, calcium channel blockers can be used to therapeutically control diseases caused by excessive fibroblast biosynthesis. Diseases characterized by fibroblast overproduction include, cirrhosis of the liver, constrictive pericarditis. Dupuytren's disease of the hand as well as other fibromatosis. While these are but a few diseases which can be treated using the methods of this invention, it should be recognized that any disease which is characterized by excessive fibroblast biosynthesis can be treated using calcium channel blockers.

The invention is further illustrated by the following Examples.

EXAMPLE 1

STUDIES ON PROTEIN AND GAG SECRETION TISSUE PREPARATION

A connective tissue model of uniaxially oriented cells and extracellular matrix was fabricated using bovine fibroblasts, rat tail tendon collagen and nutrient media. Bovine fascial fibroblasts were harvested from the thigh of freshly slaughtered 2 week old calves (Trelegan's, Cambridge Mass.) by enzymatic digestion using 0.1% type II collagenase (Worthington Biochemical Inc., Freehold, N.J.) digest ion in Dulbecco's Modified Eagle Medium (DMEM; Gibco, Grand Island, N.Y.) at 37° C. for 4 hours. The released cells were seeded onto tissue culture dishes with DMEM supplemented with 10% NuSerum (Collaborative Research. Bedford, Mass.). The media was changed every 48 hours. The cells were passaged once and then either used immediately or stored frozen in 50% calf serum/45% DMEM/5% DMSO at −100° C. When frozen cells were used they were quickly thawed, sedimented through a column of 50% serum/50% DMEM at 185 g for 3 minutes, then plated on coverslips. The media was changed after cell attachment (~4 hours).

Native type I collagen was extracted from rat tail tendon and purified using a modification of the method of Chandrakasan, G. et al., *J. Biol. Chem.* 251:6062–6067 (1976). Specifically, rat tail tendons were removed from adult Sprague-Dawley rat tails, washed in PBS and distilled water. The tendons were then placed in a solution of 0.05M (3%) acetic acid at the ratio of 200 ml per tail. The mixture was stirred for 96 hours at 8° C.

After 24 hours of stirring, the mixture was filtered through several layers of cheese cloth and then centrifuged at 12000 g (9000 rpm in Sorval GS-3 rotor) for 2 hours. The supernatant was precipitated and redissolved in cold acid multiple times to remove non-collagenous proteins. The collagen solution was sterilized in 1/1000 v/v chloroform. This procedure preserves the native structure of the collagen molecule.

Oriented tissue equivalents were made by mixing bovine fibroblasts with a 0.2% collagen solution, 20% calf serum, 10 mg/ml gentamycin solution, 5 mg/ml ascorbate in DMEM as previously described [McLeod, K. J. "Modulation of Biosynthesis by Physiologically Relevant Electric Fields" Ph.D Thesis M.I.T. 1986]. This suspension was poured into sterile culture dishes containing two sterile porous polyethylene posts held 2 centimeters apart. The dishes were placed in a cell culture incubator gassed at 5% $CO_2$ with 99% humidity. The suspension gelled at 37° C.

Over several days, the fibroblasts remodeled and consolidated the collagen gel around the fixed posts. The resultant oriented fibroblast populated collagen matrix (FPCM) formed a tissue equivalent structure which histologically resembled a ligament Oriented tissue equivalents are further described in U.S. patent application Ser. No 07/349,855, filed May 10, 1989, to R. C. Lee and D. Huang, the teachings of which are herein incorporated by reference.

Assay for Determining Biosynthetic Activity

Protein and glycosaminoglycan (GAG) biosynthesis was measured using radiolabeled precursors of protein and sulfated GAGs. Four days after casting of the FPCM, the media bathing the ligament equivalents was changed to serum free DMEM with 0.5 mM L-proline (Sigma, St. Louis, Mo.). After 12 hours, the media was changed again to fresh serum-free media supplemented with 10 µCi/ml $Na_2{}^{35}SO_4$ (NEX-041, New England Nuclear, Boston, Mass.), 10 µCi/ml L-[5-$^3$H] proline (NET-573, New England Nuclear, Boston Mass.) and 0.5 mM L-proline. The samples were bathed in the radio labeled media for 12 hours. The radiolabeled sulfate was incorporated into GAGs and radiolabeled proline into proteins, and so provide markers of sulfated GAGs and protein synthesis, respectively. Since DMEM is proline-free, the addition of non-radioactive proline ensures a relatively constant specific activity in the medium.

Effect of Calcium Channel Blockers on Biosynthesis

The effect of calcium channel blockers on protein and glycosaminoglycan (GAG) biosynthesis was measured in FPCMs under several conditions. The biosynthetic responses to calcium channel blockade were studied in FPCMs cultured in DMEM supplemented with either 5 mM glucose or 5 mM fructose. Both were studied because energy metabolism of cultured fibroblasts is primarily anaerobic when the carbohydrate energy source is glucose and predominantly aerobic when the carbohydrate source is fructose [Thilly, W. G., *Mammalian Cell Technology*, Chapter 5, Butterworth Publishers, Boston, (1986)]. In vivo fibroblasts are, however, believed to derive their energy primarily through aerobic glycolysis.

The drugs used to block calcium channels were verapamil, nifedipine and cobalt chloride. Control studies were performed to test the metabolic state of the cells in the FPCM. The effect of antimycin A, a drug which blocks oxidative phosphorylation, on biosynthesis was measured in FPCMs cultured in fructose or glucose.

Results

Energy Metabolism

Figure 1B:
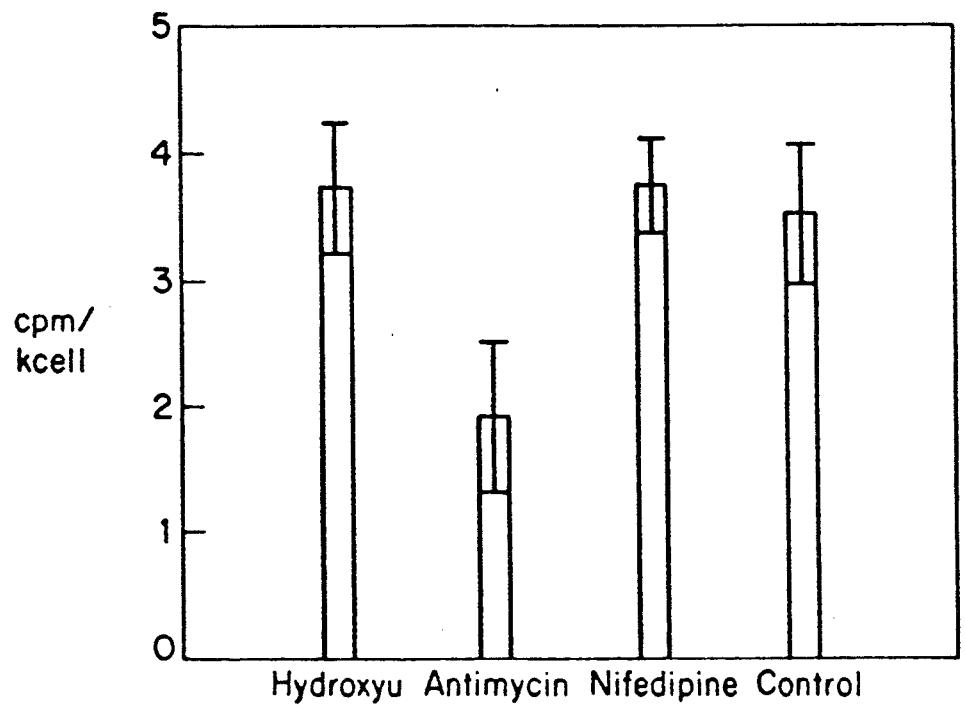
FIG. 1b is a graphic representation of the effects of hydroxyurea (7.9 mM), antimycin A (1.0 $\mu$M) and nifedipine (100 $\mu$M) on the rate of sulfate incorporation into FPCM bathed in DMEM/5.5 mM fructose.

As previously reported [Thilly, W. G., *Mammalian Cell Technology*, Chapter 5, Butterworth Publishers, Boston, (1986), differences between cellular energy metabolism of fibroblasts provided with glucose or fructose as energy substrates were observed. The effects of antimycin A on both incorporation of proline into extracellular matrix protein and incorporation of sulfate into extracellular matrix glycosaminoglycans over a 12 hour period was measured in FPCMs bathed in DMEM/5.5 mM fructose and their results are shown in FIGS. 1a and 1b, respectively. Antimycin A had little effect on proline incorporation with FPCMs provided with glucose. In contrast. antimycin A caused a substantial reduction in the rate of proline incorporation into the extracellular matrix in FPCMs provided with fructose.

Protein and Glycosaminoglycan Biosynthesis

Figure 2A:
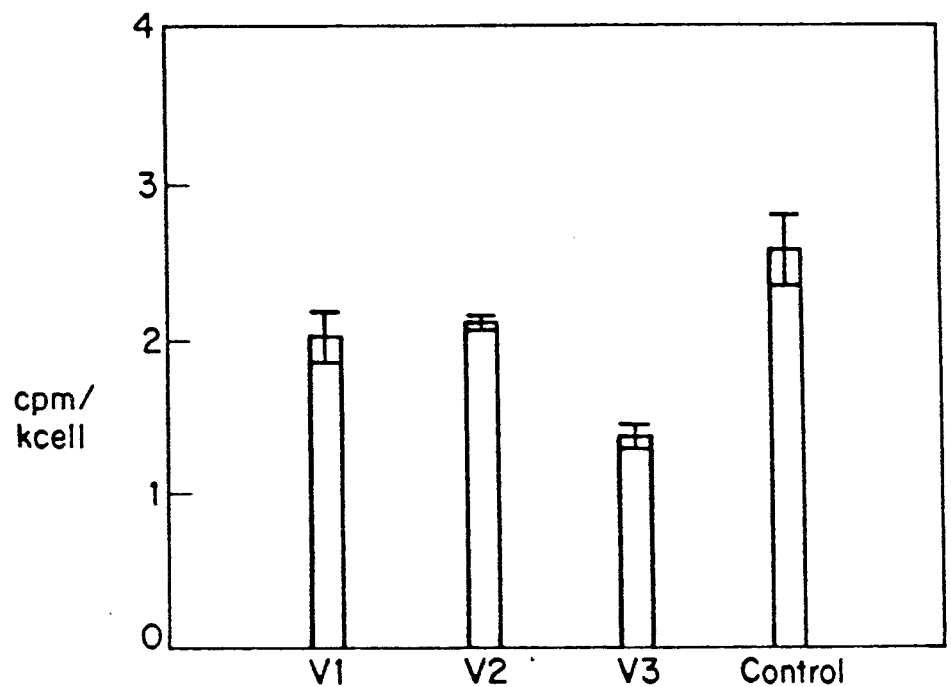
FIGS. 2a and 2b are graphic representations of the dose-dependent effect of verapamil on the rate of proline incorporation in FPCM bathed in DMEM/5.5 mM glucose and fructose, respectively. V1 represents 1 $\mu$M verapamil, V2 represents 10 $\mu$M verapamil and V3 represents 100 $\mu$M verapamil.
Figure 2B:
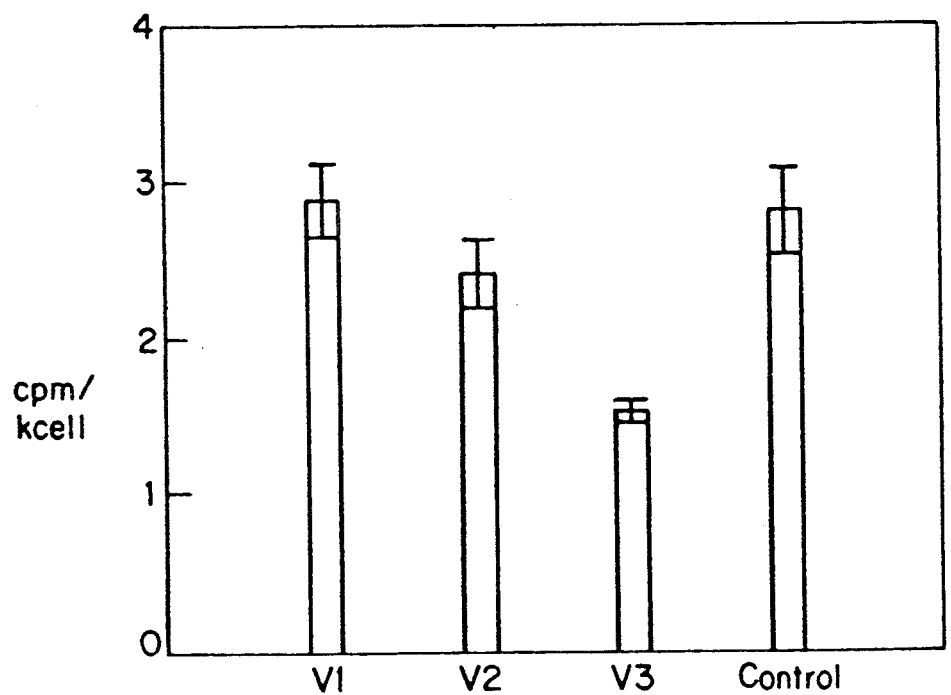

When the effect of the carbohydrate source on the rate of biosynthesis of protein and glycosaminoglycan was examined in FPCMs bathed in DMEM/0.5 mM cold proline, no difference was observed between control FPCMs in glucose or fructose (FIG. 2). There was a dose-dependent effect of verapamil on protein incorporation. However, the biosynthetic response to calcium channel blockaid was observed to depend on the type of calcium channel blocker used and whether the carbohydrate source was glucose or fructose.

Figure 3A:
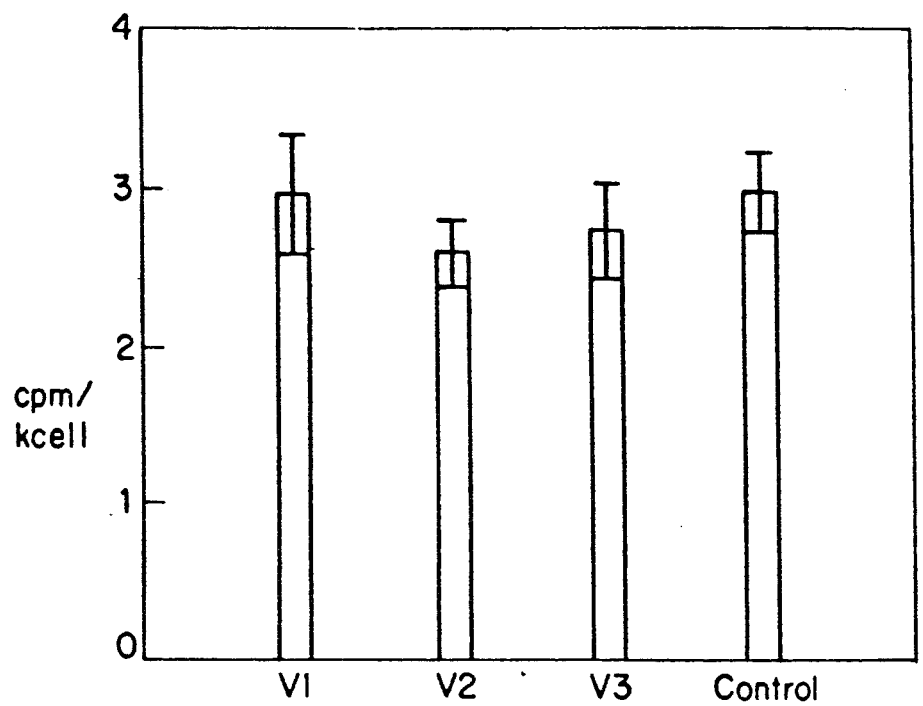
FIGS. 3a and 3b are graphic representations of the effects of verapamil on the rate of sulfate incorporation into glycosaminoglycans in FPCM bathed in DMEM/5.5 mM glucose and fructose, respectively. V1 represents 1 $\mu$M verapamil, V2 represents 10 $\mu$M verapamil and V3 represents 100 $\mu$M verapamil.
Figure 3B:
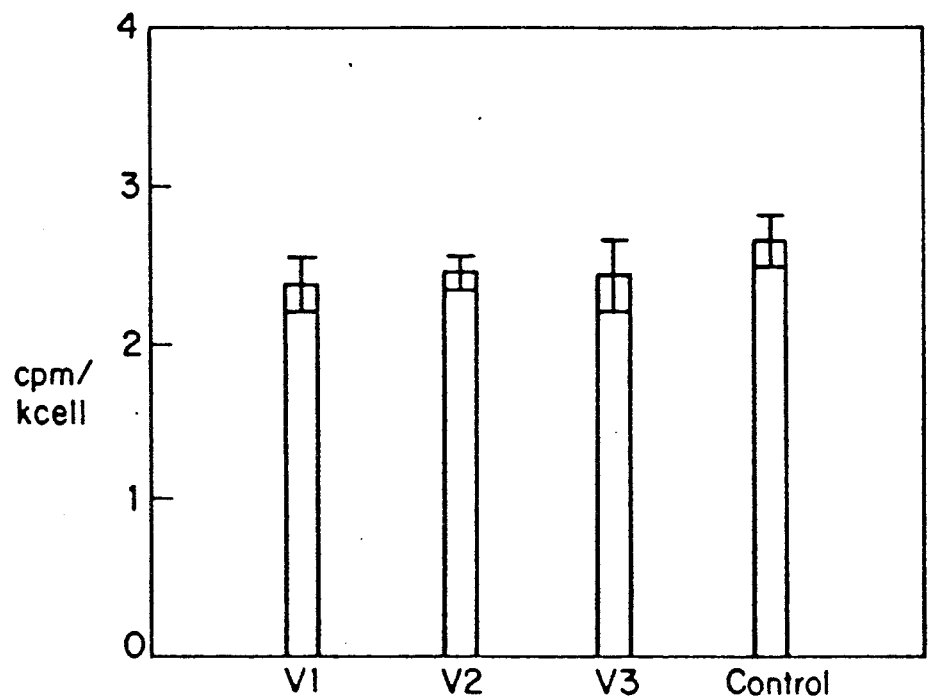

Verapamil retarded the incorporation of proline into the extracellular matrix in the presence of either glucose or fructose (FIG. 2). However, fibroblasts appeared to be more sensitive to verapamil when glucose was used as the metabolic energy source. Verapamil at 100 µM concentration reduced the incorporation by almost 50% in FPCMs provided with either glucose or fructose. Verapamil had no significant effect on sulfated glycosaminoglycan biosynthesis, even at concentrations of 100 µM (FIG. 3). The lack of effect on GAG biosynthesis incorporation indicated that the verapamil did not reduce cell viability.

In equimolar concentrations, nifedipine caused a larger reduction of proline incorporation than verapamil. As for verapamil, nifedipine at 100 µM concentration had no effect on GAG biosynthesis.

The rates of proline and sulfated glycosaminoglycan incorporation in fibroblast populated collagen matrices bathed in DMEM/5.5 mM glucose or fructose and a calcium channel blocker are shown in Table I. 50 mg/ml of cobalt chloride had a profound effect in reducing the rate of protein biosynthesis and increasing the rate of secretion of sulfated glycosaminoglycans, as compared with the effects of verapamil.

TABLE I

Rates of Incorporated Proline and Sulfate for Cultured Bovine Fibroblasts in FPCL in DMEM with Glucose or Fructose plus Calcium Channel Blockers

| | Glucose (5.5 mM) | | Fructose (5.5 mM) | |
|---|---|---|---|---|
| | Proline (cpm/1 × $10^3$ cells) | Glycosamino glycans sulfate | Proline (cpm/1 × $10^3$ cells) | Glycosamino glycans sulfate |
| Control | 1.00 ± 0.04 (16) | 1.00 ± 0.03 (16) | 1.00 ± 0.05 (16) | 1.00 ± 0.04 (16) |
| Verapamil (1 μM) | 0.85 ± 0.02 (16) | 1.02 ± 0.03 (16) | 1.02 ± 0.02 (16) | 1.00 ± 0.04 (16) |
| Cobalt (50 ug/ml) | 0.79 ± 0.01 (16) | 1.14 ± 0.03 (16) | 0.90 ± 0.03 (16) | 1.01 ± 0.02 (16) |

EXAMPLE 2

STUDIES ON EXOCYTOSIS HUMAN FIBROBLAST CELL CULTURE

Human neonatal foreskin fibroblasts were harvested from newborns at the time of circumcision at the Brigham and Woman's Hospital. The samples were initially placed in antibiotic supplemented Dulbecco's Modified Eagles Media (DMEM) then incubated in trypsin for 20 minutes to remove the surface epithelial layer. The tissue was then washed in Phosphate-Buffered Saline (PBS) solution, then centrifuged at 180 g for 5 minutes to separate the epidermal cells. The dermis was minced then subjected to 0.1% type II collagenase (Worthington Biochemical Inc., Freehold. N.J.) digestion in DMEM for 4 hours. The released cells were seeded onto tissue culture dishes with DMEM supplemented with 10% NuSerum (Collaborative Research, Bedford, Mass.). The media was changed every 48 hours. The cells were passed once and then were either used immediately or stored frozen in 50% serum/45% DMSO at −100° C. When frozen cells were used they were quickly thawed, sedimented through a column of 50% serum/50% DMEM at 185 g for 3 minutes, then plated on coverslips. The media was changed after cell attachment (~4 hours).

Quantification of Dye Release

To determine if the rate of fluid phase exocytosis was modulated by calcium channel blockers, the rate of exocytosis in human fibroblasts was measured using the rate of release of Lucifer yellow labeled dextran (LYD, M.W. 10,000) (Molecular Probes Inc., Portland, Oreg.), from vesicles in the cytoplasm of human foreskin fibroblasts. The LYD was loaded into cells by fluid phase pinocytosis (endocytosis) in the absence of serum. The intracellular location and transport of the dye was monitored under control and experimental conditions using video image analysis.

$P_2$–$P_5$ fibroblast cells were harvested from monolayer by brief 1x trypsin and ethylenediamine tetraacetic acid (EDTA) digestion, plated on glass coverslips and allowed to become 50% confluent. Cell laden coverslips (CLCS) were bathed in DMEM supplemented with 5 mg/ml Lucifer Yellow CH Dextran (LYD) for 12 hours under standard conditions. The CLCS were then washed five times in PBS at 37° C. to remove extracellular LYD. then placed in 60 mm sterile cell culture dishes. The dishes contained serumfree DMEM at 37° C. supplemented with either verapamil (10 μM), or no drug (control). The dishes were returned to the 5% $CO_2$ gassed incubator. Two CLCS were removed from each of the dishes after 0, 2, 4 and 6 hours. They were quickly immersed in neutral buffered formalin at 8° C. allowed 20 minutes to fix, then the CLCS were mounted on glass microscope slides. The mounting solution was 50% glycerol. NaF phenylaminediamine.

Each cell to be analyzed was placed in the center position within the field of view. The LY fluorescence was excited by filtered 100 watt mercury arc lamp illumination. The excitation was filtered with an interference filter with a bandpass of 460–485 nm. The emission was collected with a 40x objective and passed through a 515 nm barrier filter. The emission was recorded with a video camera head with a chalnicon tube, digitized and stored by a Hamamatsu video image processor under the control of a VaxStation II computer. This procedure was repeated under phase illumination so that the boundaries of the cell could be accurately identified by phase contrast. A software program located the boundaries of the cell by identifying pixels with intensity values more than two standard deviations below the mean background pixel intensity in a manually chosen background area.

To quantify the average intensity in the cell cytoplasm, the mean background value ($B_m$) was subtracted from the entire image including the pixel values in the cell ($P_i$). Since the background intensity could be used as a measure of the excitation intensity, the net pixel values within the boundaries of the cell were normalized to $B_m$. The normalized pixel values were then summed, and that sum was normalized to the area of the cell (A). This result was termed the intensity of the cell $I_c$:

$$I_c = \Sigma_i(P_i - B_m)/B_m A$$

$I_c$ was determined for each of the 50 cells, 25 from each of two simultaneously-removed coverslips. The standard deviation and means were then calculated. The mean for two coverslips was plotted at each time point (2, 4 and 6 hours). This process was carried out for both the experimentals and controls at each time point.

Results

Exocytosis

Figure 4:
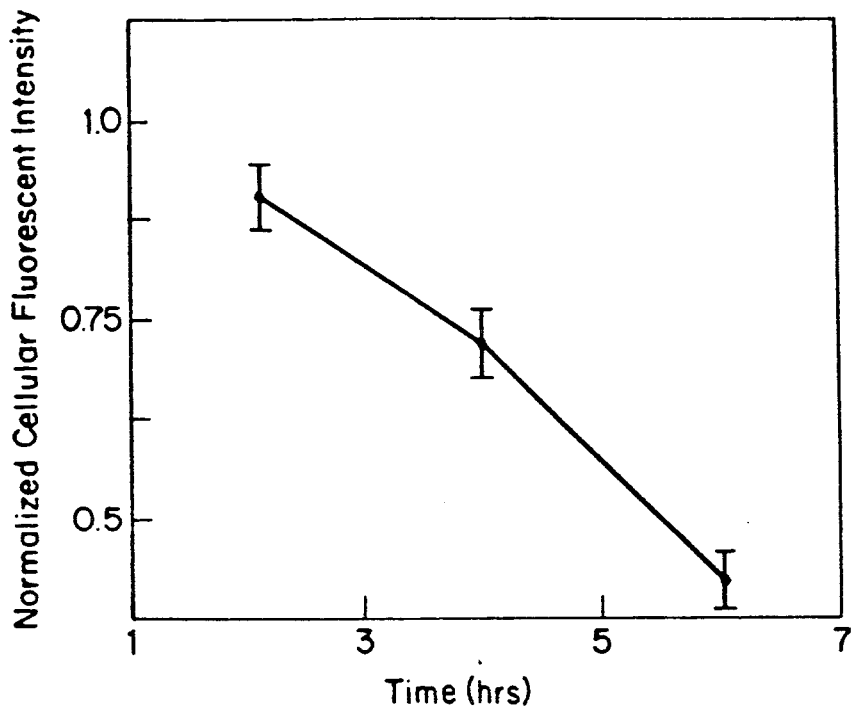
FIG. 4 is a graphic representation of the rate of exocytosis in human dermal fibroblasts in monolayer culture as a function of cellular fluorescence verses exposure time. Release of Lucifer Yellow CH from secretory vesicles in fibroblasts to the extracellular space is indicated by cellular fluorescence vs. time after dye loading. Loss of fluorescence occurs via exocytosis. Approximately 55% of the dye is secreted in 6 hours.
Figure 5:
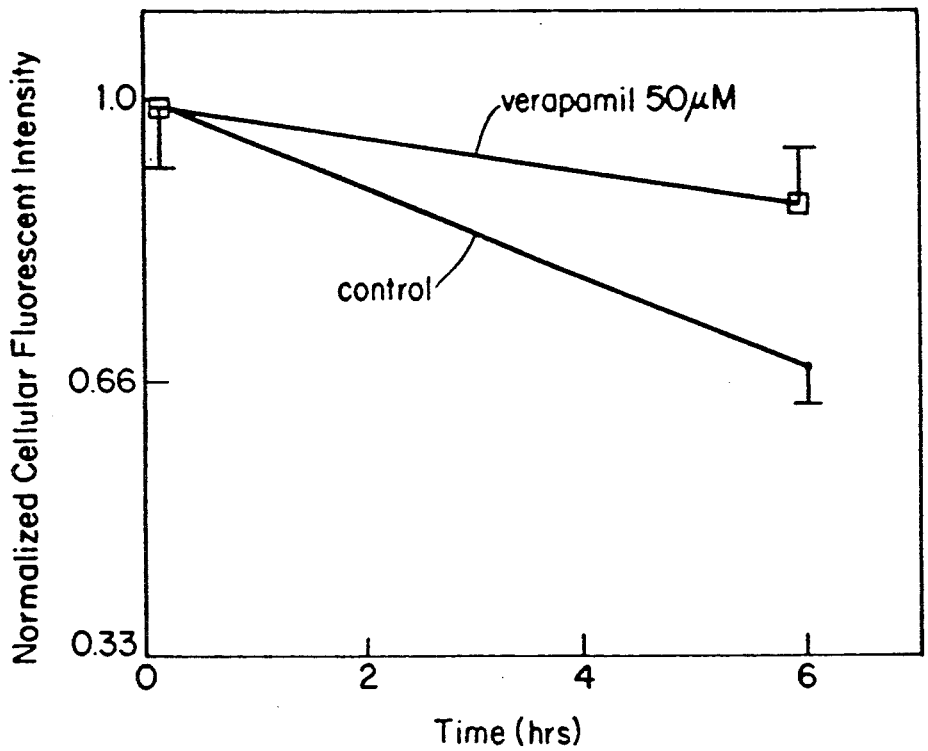
FIG. 5 is a graphic representation of the effect of calcium antagonist verapamil (50 $\mu$M) on release of Lucifer Yellow CH from human dermal fibroblasts in monolayer culture. Retardation of exocytosis is demonstrated.

Exocytosis was observed to proceed at a near constant rate over a six hour period of observation in human dermal fibroblasts in monolayer culture (FIG. 4). The rate of exocytosis of Lucifer yellow dextran was found to be sensitive to plasma membrane calcium channel function. Both verapamil (10 μM) and nifedipine (100 μM) were found to significantly retard exocytosis over a six hour period in these cells (FIG. 5 and Tables II and III). These results clearly demonstrate that exocytosis in human fibroblasts can be regulated. In FIG. 5, the controls are represented by the filled circles and verapamil is represented by the squares. Tables II and III show the retardation of exocytosis in human dermal fibroblasts by calcium channel blockers, verapamil (50 $\mu$M) and nifedipine (1 $\mu$M), respectively.

TABLE II

Effect of Verapamil on Exocytosis Response

| Stimulus | Exposure Time (hours) | Average Intensity | Standard Error | Intensity Difference | p value |
|---|---|---|---|---|---|
| Control | 0 | 855 | 38 | | |
| | 6 | 691 | 23 | | |
| Verapamil: 50 $\mu$M | 6 | 793 | 35 | 14.8% | p < 0.02 |

TABLE III

Effect of Nifedipine on Exocytosis Response

| Stimulus | Exposure Time (hours) | Average Normalized Intensity | Standard Error | p value |
|---|---|---|---|---|
| Control | 0 | .58 | .029 | |
| | 4 | .54 | .029 | |
| | 6 | .36 | .015 | |
| Nifedipine: 1 $\mu$M | 4 | .58 | .029 | p > 0.05 |
| | 6 | .49 | .047 | p < 0.03 |

Equivalents

Those skilled in the art will recognize, or be able to ascertain using no more than routine experimentation, many equivalents to the specific embodiments of the invention described specifically herein. Such equivalents are intended to be encompassed in the scope of the following claims.

I claim:

1. A method for reducing scar tissue associated with hypertrophic wound healing disorders, comprising administering an effective amount of a calcium channel blocker locally to a hypertrophic scar site for a period of time sufficient to minimize or essentially eliminate the scar.

2. The method of claim 1 wherein the calcium channel blocker is admixed with a pharmaceutically acceptable vehicle.

3. The method of claim 2 wherein the calcium channel blocker is selected from the group consisting of nifedipine, hydropyridine, verapamil, cobalt chloride and biologically acceptable salts of cobalt.

4. The method of claim 1 wherein the step of administering is by injecting the calcium channel blocker into the wound.

5. The method of claim 1 wherein the step of administering is by topically applying the calcium channel blocker onto the scar.

6. The method of claim 1 wherein the step of administering is by incorporating the calcium channel blocker into a controlled releasing polymer.

7. A method for reducing fibromastosis, comprising administering an effective amount of a calcium channel blocker locally to a fibromastosis for a period of time sufficient to significantly reduce or essentially eliminate the fibromastosis.

8. The method of claim 7 wherein the calcium channel blocker is admixed with a pharmaceutically acceptable vehicle.

9. The method of claim 7 wherein the calcium channel blocker is selected from the group consisting of nifedipine, hydropyridine, verapamil, cobalt chloride and biologically acceptable salts of cobalt.

10. The method of claim 7 wherein the step of administering is by injecting the calcium channel blocker into the wound.

11. The method of claim 7 wherein the step of administering is by topically applying the calcium channel blocker onto the scar.

12. The method of claim 7 wherein the step of administering is by incorporating the calcium channel blocker into a controlled releasing polymer.

* * * * *